United States Patent [19]

Varma

[11] 4,219,488
[45] Aug. 26, 1980

[54] PROCESS FOR PREPARING STEROIDAL [16α,17-b]NAPHTHALENO-21-CARBOXYLIC ACID ESTERS

[75] Inventor: Ravi K. Varma, Belle Mead, N.J.

[73] Assignee: E. R. Squibb & Sons, Inc., Princeton, N.J.

[21] Appl. No.: 33,357

[22] Filed: Apr. 26, 1979

[51] Int. Cl.$^2$ .............................................. C07J 5/00
[52] U.S. Cl. ............................ 260/397.1; 260/397.3; 260/397.45; 424/243
[58] Field of Search .............. 260/397.1, 397.3, 397.45

[56] References Cited

U.S. PATENT DOCUMENTS 3,501,513   3/1970   Bacso .............................. 260/397.47
3,944,584   3/1976   Chao et al. ...................... 260/397.47

Primary Examiner—Elbert L. Roberts
Attorney, Agent, or Firm—Lawrence S. Levinson; Donald J. Barrack

[57] ABSTRACT

Steroidal [16α,17-b]naphthaleno-21-carboxylic acid esters can be prepared from 21-hydroxy-$\Delta^{16}$-steroids by converting the starting steroid to a 21-carboxylic acid ester -$\Delta^{16}$-steroid and then fusing the tetrahydronaphthalene ring to the 16,17-positions of the intermediate.

9 Claims, No Drawings

PROCESS FOR PREPARING STEROIDAL [16α,17-b]NAPHTHALENO-21-CARBOXYLIC ACID ESTERS

RELATED APPLICATION

Copending U.S. patent application Ser. No. 919,020, filed June 26, 1978, now U.S. Pat. No. 4,164,504, issued Aug. 14, 1979, discloses inter alia, steroid products having the formula

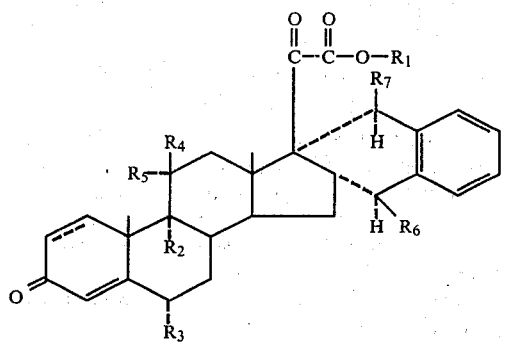

and steroid intermediates having the formulas

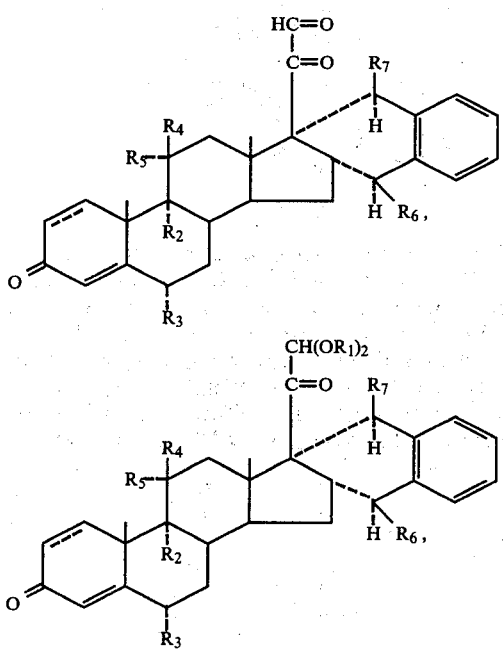

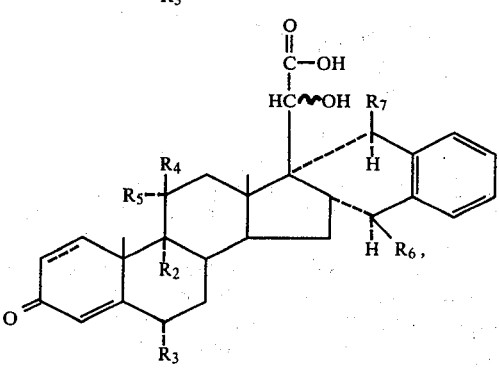

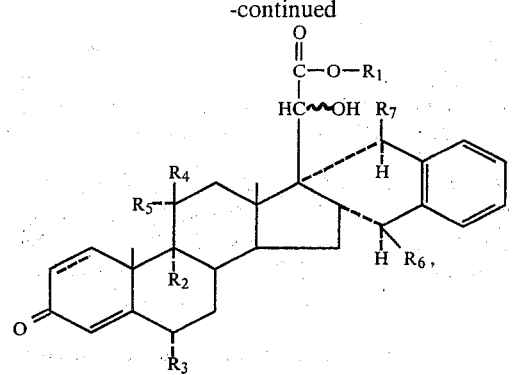

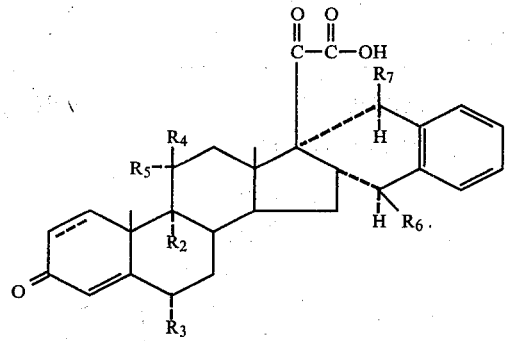

In the above formulas, the symbols are as defined hereinafter. The application teaches the preparation of the above steroid products utilizing as a starting material the corresponding 21-hydroxy-steroidal [16α,17-b]naphthalenes. The starting steroid can be oxidized in an alcohol ($R_1$—OH) solvent to a mixture of the corresponding aldehyde (formula II) and acetal (formula III) or to the corresponding 20-hydroxy-21-carboxylic acid (formula IV) or to the 20-hydroxy-21-carboxylic acid ester (formula V). Reacting a mixture of steroids of formulas II and III with an inorganic cyanide catalyst, an oxidizing agent, an inert solvent, an alcohol and an acid yields the product of formula I.

Copending U.S. patent application Ser. No. 33,351, filed Apr. 26, 1979, discloses a process for preparing steroidal [16α,17-d]cyclohexene-21-carboxylic acid esters utilizing intermediates disclosed herein.

BACKGROUND OF THE INVENTION

Antiinflammatory activity, topical and systemic, is exhibited by many steroids of the pregnene series. More specifically, steroidal[16α,17-b]naphthalenes having the formula

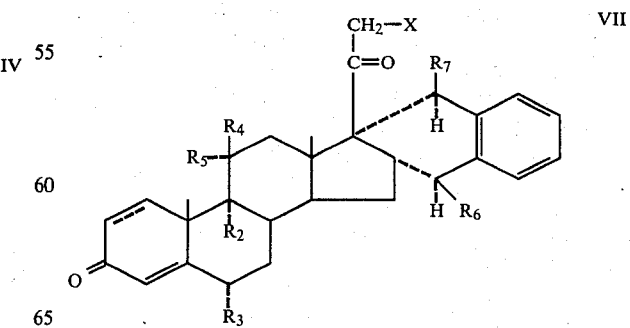

wherein X is hydrogen, hydroxy, acyloxy or halogen, and the "R groups" are as defined hereinafter, are disclosed as having topical and systemic antiinflammatory activity; see, for example, U.S. Pat. No. 3,937,720 issued Feb. 10, 1976.

The prior art also discloses various pregnene-21-oic acid derivatives and corresponding esters as having topical antiinflammatory activity, while being essentially inactive systemically. Exemplary disclosures are U.S. Pat. No. 3,956,347, issued May 11, 1976; U.S. Pat. No. 3,919,421, issued Nov. 11, 1975; U.S. Pat. No. 4,049,804, issued Sept. 30, 1977; and Laurent et al., Journal of Steroid Biochemistry, 6: 185–192 (1975). One such pregnene derivative, fluocortin butyl ester (6α-fluoro-11β-hydroxy-16α-methyl-3,20-dioxopregna-1,4-diene-21-oic acid, butyl ester) has drawn particular attention and interest. Monder et al., Journal of Steroid Biochemistry, 8: 897–908 (1977), discuss the synthesis of carboxylic acid derivatives of steroids, and the existence of these derivatives as metabolites of steroids.

BRIEF DESCRIPTION OF THE INVENTION

Steroids having the formula

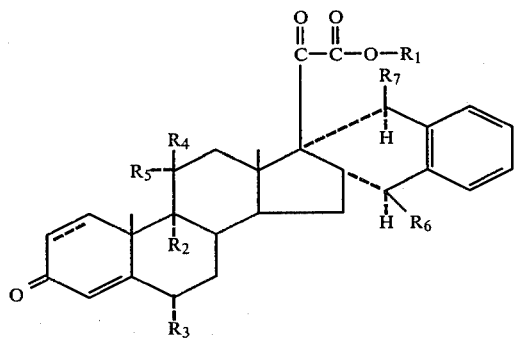

can be prepared from the corresponding 21-hydroxy-$\Delta^{16}$-steroid having the formula

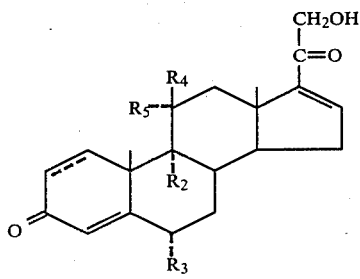

by first converting the 21-hydroxy group to a 21-carboxylic acid ester group and then fusing the tetrahydronaphthalene group in the 16,17-position. In formulas I and VIII, and throughout the specification, the symbols are as defined below:

$R_1$ is alkyl of 1 to 10 carbon atoms, aryl, or arylalkyl;
$R_2$ is hydrogen or halogen;
$R_3$ is hydrogen, fluorine or methyl;
$R_4$ is chlorine, fluorine or hydroxy and $R_5$ is hydrogen or $R_4$ and $R_5$ together are =O; and
$R_6$ and $R_7$ are the same or different and are hydrogen, alkyl, alkoxy, carboalkoxy, formyl,

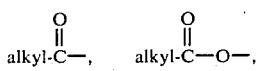

hydroxy, halogen, phenyl or cyano with the proviso that when $R_6$ and $R_7$ are different, one of $R_6$ and $R_7$ is hydrogen.

The dotted lines in the 1,2-position of the steroids of this invention represent the optional presence of ethylenic unsaturation.

The terms "alkyl" and "alkoxy", as used throughout the specification (unless otherwise defined), refer to both straight and branched chain groups having 1 to 6 carbon atoms.

The term "aryl", as used throughout the specification, refers to phenyl or phenyl substituted with one or more halogen, alkyl and alkoxy groups.

The term "halogen", as used throughout the specification, refers to fluorine, chlorine, bromine and iodine.

DETAILED DESCRIPTION OF THE INVENTION

The 21-hydroxy-$\Delta^{16}$-steroids of formula VIII, which form the starting point for the process of this invention, or the corresponding 21-acyloxy steroids are known in the art. The 21-acyloxy steroids are readily converted to the corresponding 21-hydroxy steroids using conventional techniques.

A steroid of formula VIII can be oxidized to the corresponding aldehyde having the formula

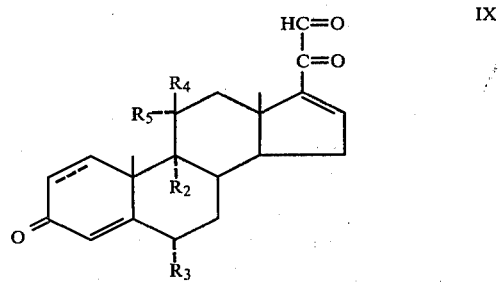

using oxygen (or air) and a catalyst such as copper acetate. The reaction can be run in an alcohol solvent.

If the above described oxidation reaction is carried out in the presence of oxygen (e.g., by bubbling air through the reaction mixture), the reaction will generally yield, in addition to a steroidal-21-aldehyde of formula IX, the corresponding steroidal-21-acetal formed with the alcohol solvent ($R_1$—OH); i.e., a steroid having the formula

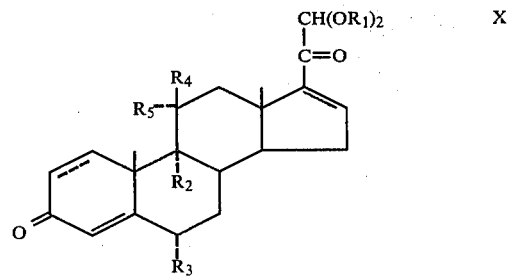

The oxidation reaction will generally be completed within a relatively short period of time, i.e., about 1 hour.

If the above described reaction is allowed to proceed for an extended period of time, e.g., more than about 24 hours, the major product will be the 20-hydroxy-21-carboxylic acid ester having the formula

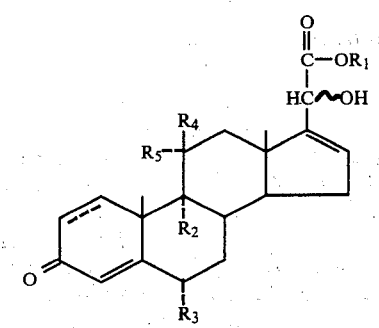

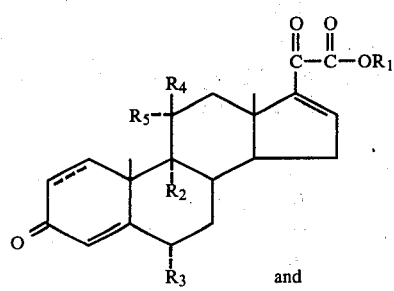

and

If water is present as a co-solvent in the oxidation reaction, and the reaction is allowed to proceed for an extended period of time, in addition to the 20-hydroxy-21-carboxylic acid ester of formula XI, the corresponding 20-hydroxy-21-carboxylic acid will be produced; i.e., a steroid having the formula

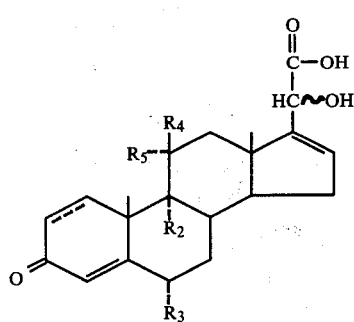

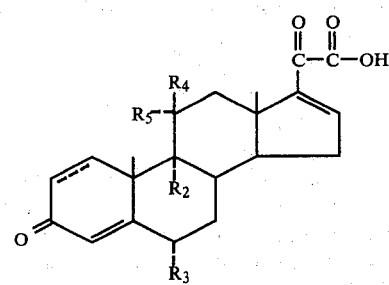

The steroids of formulas XI and XII exist as mixtures of the 20α- and 20β-hydroxy-steroids. Reaction of a mixture of a steroidal-21-aldehyde of formula IX and the corresponding steroidal-21-acetal of formula X with a mixture of (i) an inorganic cyanide catalyst (e.g., an alkali metal cyanide such as potassium cyanide); (ii) an oxidizing agent, e.g., a heavy metal oxide such as activated manganese dioxide or lead dioxide; (iii) an inert solvent, e.g., a halogenated hydrocarbon solvent such as dichloromethane or chloroform; (iv) a primary or secondary alcohol, $R_1'$-OH (throughout the specification $R_1'$ is any nontertiary $R_1$ group); and (v) an acid, e.g., acetic acid, which serves to neutralize the alkali cyanide catalyst; yields a steroid having the formula

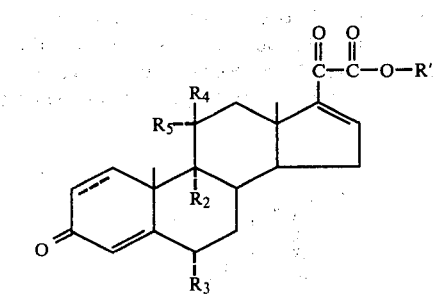

The 20α-and-20β-hydroxysteroids of formulas XI and XII can be oxidized to obtain the corresponding 20-ketosteroids, having the respective formulas Exemplary of suitable oxidizing agents are manganese dioxide and chromium dioxide. In the instance wherein the 20α- and 20β-hydroxysteroids being oxidized have an 11β-hydroxy substituent, the steroids of formulas XIV and XV will be mixtures of 11β-hydroxy and 11-keto steroids.

The intermediates of formula XIV can also be prepared by esterification of the corresponding steroidal-21-oic acid of formula XV. (A steroid of formula XV can be prepared as described above, or alternatively, by saponification of a corresponding steroidal-21-oic acid ester of formula XIV.)

Still another route for the preparation of the intermediates of formula XIV wherein $R_1$ is a non-tertiary group is the transesterification of another ester of formula XIII or XIV. The starting steroid is reacted with the appropriate alcohol in the presence of a basic alkoxide (e.g., sodium ethoxide or aluminum isopropoxide) or, preferably, a source of cyanide ion (e.g., an alkali metal cyanide such as sodium cyanide or potassium cyanide) to yield the transesterification product.

A steroid of formula XIII or XIV can be converted to the corresponding product of formula I by reacting it with a benzocyclobutene having the formula

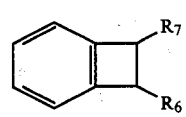

The reaction can be run neat or in an inert solvent, e.g., o-dichlorobenzene or diethylbenzene. Preferably the reaction will be run neat, in an inert atmosphere, at temperatures up to the boiling point of the solution. A free radical inhibitor may be added to the mixture.

The intermediates of formulas IX, X, XI, XII, XIII, XIV and XV are novel compounds that form an integral part of this invention.

The following examples are specific embodiments of this invention.

EXAMPLE 1

9-Fluoro-1',2',3',4'-tetrahydro-11β-hydroxy-3,20-dioxopregna-1,4-dieno[16α,17-b]naphthalene-21-oic acid, methyl ester

(A)

9-Fluoro-11β-hydroxy-3,20-dioxopregna-1,4,16-triene-21-carboxaldehyde and 9-fluoro-11β-hydroxy-21-dimethoxypregna-1,4,16-triene-3,20-dione A solution of 9-fluoro-11β,21-dihydroxypregna-1,4,16-triene-3,20-dione (1.7 g) is dissolved in methanol (300 ml) by warming and the solution is cooled to room temperature. Copper acetate (100 mg) is added and a stream of air is passed into the solution under stirring. In about 20 minutes the starting material disappears to give less polar compounds as indicated by thin layer chromatography. The solution is then evaporated in vacuo, the residual solid is washed successively with a dilute ammonium chloride solution and water and is dried to afford an essentially equimolar mixture (1.9 g) of the title aldehyde (as its hydrate) and the title acetal as indicated by the NMR spectrum. When dried in vacuo (125°-130° C., 0.5 mm of Hg) for 2.0 hours, this material is converted into an essentailly equimolar mixture (1.77 g) of the title aldehyde and acetal as shown by NMR and IR spectra.

(B)

9-Fluoro-11β-hydroxy-3,20-dioxopregna-1,4,16-trieno-21-oic acid, methyl ester

To a stirred solution of the mixture of aldehyde and acetal prepared in part A (1.75 g), in a mixture of anhydrous dichloromethane (100 ml) and anhydrous methanol (20 ml) is added successively activated manganese dioxide (4.0 g), potassium cyanide (500 mg) and glacial acetic acid (0.5 ml). In less than 1.0 hour, the starting materials disappear to give essentially a single less polar compound as indicated by thin layer chromatography. The reaction mixture is filtered through a bed of diatomaceous earth and the filter cake is washed with several small portions of a warm mixture of dichloromethane-methanol. The filtrate and the washings are combined and evaporated to a solid residue which is washed with water and dried. Crystallization of the resulting material from methanol-dichloromethane (with evaporative removal of dichloromethane) yields 1.4 g of the title compound, melting point 284°-286° C.

(C)

9-Fluoro-1',2',3',4'-tetrahydro-11β-hydroxy-3,20-dioxopregna-1,4-dieno[16α,17-b]naphthalene-21-oic acid, methyl ester A solution of 9-fluoro-11β-hydroxy-3,20-dioxopregna-1,4,16-trieno-21-oic acid, methyl ester (100 mg) in benzocyclobutene (5.0 ml) containing 4,4'-thiobis-6-t-butyl-m-cresol (6.0 mg) is refluxed under an atmosphere of nitrogen for 10 hours; a solid separates from the solution. The unreacted benzocyclobutene is recovered by vacuum distillation and the pot residue is recrystallized from methanol-dichloromethane (by evaporative removal of the dichloromethane) to yield the title compound, melting point 325°-326° C. (discoloration starts from about 295° C).

EXAMPLE 2

9-Fluoro-11β-hydroxy-3,20-dioxopregna-1,4,16-trieno-21-oic acid

A solution of 9-fluoro-11β-hydroxy-3,20-dioxopregna-1,4,16-trieno-21-oic acid, methyl ester (100 mg; see Example 1B) in a mixture of methanol (15 ml) and tetrahydrofuran (15 ml) is stirred with 3 M sodium hydroxide (1.0 ml) under a nitrogen atmosphere for 2.0 hours. The mixture is then acidified with 5% hydrochloric acid and evaporated to a residue. The residue is washed with water and crystallized from chloroform-methanol to yield the title compound. This material turns black when heated to 400° C., but does not melt.

The steroid of this Example can be esterified using conventional techniques and then reacted with a benzocyclobutene as described in Example 1C to yield a product of formula I.

What is claimed is:

1. A process for converting a steroid having the formula

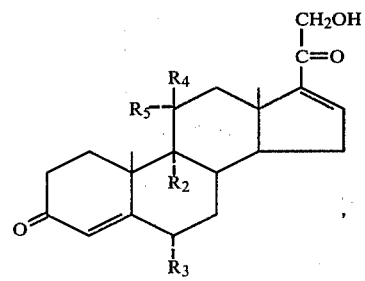

or the 1,2-dehydro derivative thereof, to a steroid having the formula

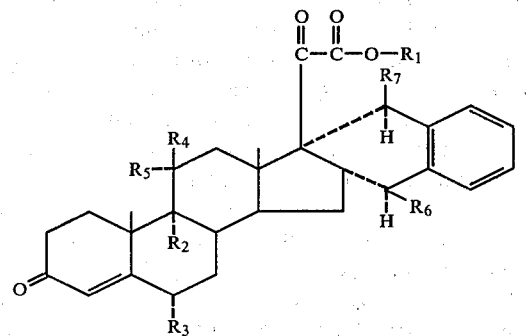

or the 1,2-dehydro derivative thereof, which comprises first converting the 21-hydroxy group of the starting steroid to a 21-carboxylic acid ester group and then reacting the resulting 21-carboxylic acid ester-Δ16-steroid intermediate with a benzocyclobutene having the formula

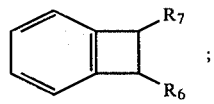

wherein
R1 is alkyl of 1 to 10 carbon atoms, aryl or arylalkyl;
R2 is hydrogen or halogen;
R3 is hydrogen, fluorine or methyl;

$R_4$ is chlorine, fluorine or hydroxy and $R_5$ is hydrogen, or $R_4$ and $R_5$ together are =O; and $R_6$ and $R_7$ are the same or different and are hydrogen, alkyl, alkoxy, carboalkoxy, formyl,

hydroxy, halogen, phenyl or cyano with the proviso that when $R_6$ and $R_7$ are different, one of $R_6$ and $R_7$ is hydrogen.

2. A steroid having the formula

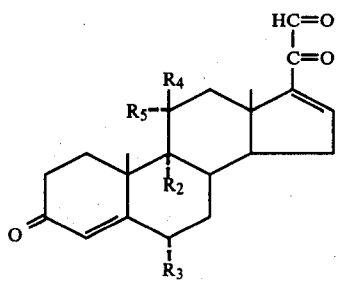

or the 1,2-dehydro derivative thereof, wherein $R_2$ is hydrogen or halogen; $R_3$ is hydrogen, fluorine or methyl; and $R_4$ is chlorine, fluorine or hydroxy and $R_5$ is hydrogen, or $R_4$ and $R_5$ together are =O.

3. A steroid in accordance with claim 2 wherein $R_2$ is fluorine, $R_3$ is hydrogen, $R_4$ is hydroxy and $R_5$ is hydrogen.

4. A steroid having the formula

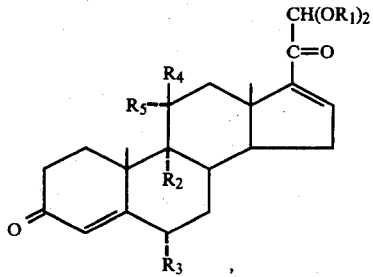

or the 1,2-dehydro derivative thereof, wherein $R_1$ is alkyl of 1 to 10 carbon atoms, aryl or arylalkyl; $R_2$ is hydrogen or halogen; $R_3$ is hydrogen, fluorine or methyl; and $R_4$ is chlorine, fluorine or hydroxy and $R_5$ is hydrogen, or $R_4$ and $R_5$ together are =O.

5. A steroid in accordance with claim 4 wherein $R_2$ is fluorine, $R_3$ is hydrogen, $R_4$ is hydroxy and $R_5$ is hydrogen.

6. A steroid having the formula

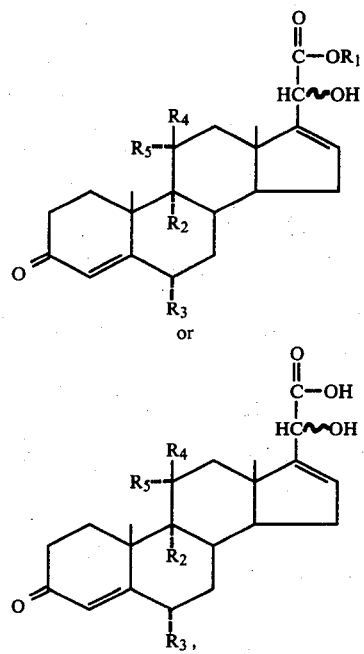

or the 1,2-dehydro derivative thereof, wherein $R_1$ is alkyl of 1 to 10 carbon atoms, aryl or arylalkyl; $R_2$ is hydrogen or halogen; $R_3$ is hydrogen, fluorine or methyl; $R_4$ is chlorine, fluorine or hydroxy and $R_5$ is hydrogen, or $R_4$ and $R_5$ together are =O.

7. A steroid in accordance with claim 6 wherein $R_2$ is fluorine, $R_3$ is hydrogen, $R_4$ is hydroxy and $R_5$ is hydrogen.

8. A steroid having the formula

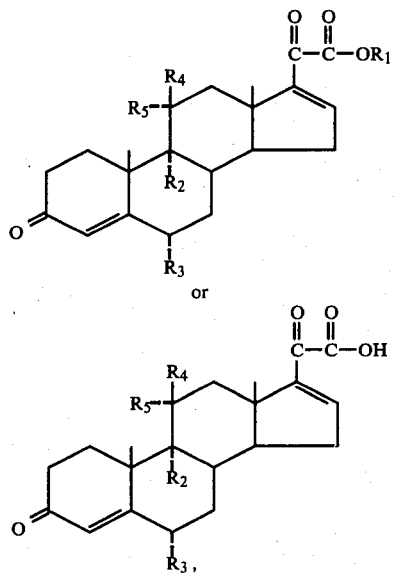

or the 1,2-dehydro derivative thereof, wherein $R_1$ is alkyl of 1 to 10 carbon atoms, aryl or arylalkyl; $R_2$ is hydrogen or halogen; $R_3$ is hydrogen, fluorine or methyl; $R_4$ is chlorine, fluorine or hydroxy and $R_5$ is hydrogen, or $R_4$ and $R_5$ together are =O.

9. A steroid in accordance with claim 8 wherein $R_2$ is fluorine, $R_3$ is hydrogen, $R_4$ is hydroxy and $R_5$ is hydrogen.

* * * * *